United States Patent
Rose-Petruck et al.

(10) Patent No.: US 10,307,527 B2
(45) Date of Patent: Jun. 4, 2019

(54) PROTEIN-BASED NANOBUBBLE X-RAY IMAGING METHOD AND AGENT

(71) Applicants: Brown University, Providence, RI (US); MONTANA STATE UNIVERSITY, Bozeman, MT (US)

(72) Inventors: Christoph Rose-Petruck, Barrington, RI (US); Trevor Douglas, Bloomington, IN (US); Danielle Rand, Walpole, MA (US); Masaki Uchida, Bloomington, IN (US)

(73) Assignees: Brown University, Providence, RI (US); Montana State University, Bozeman, MT (US)

( * ) Notice: Subject to any disclaimer, the term of this patent is extended or adjusted under 35 U.S.C. 154(b) by 0 days.

(21) Appl. No.: 14/692,075

(22) Filed: Apr. 21, 2015

(65) Prior Publication Data

US 2015/0297756 A1 Oct. 22, 2015

Related U.S. Application Data

(60) Provisional application No. 61/981,945, filed on Apr. 21, 2014.

(51) Int. Cl.
*A61B 6/06* (2006.01)
*A61M 5/00* (2006.01)
(Continued)

(52) U.S. Cl.
CPC .............. *A61M 5/007* (2013.01); *A61B 6/481* (2013.01); *A61K 49/0461* (2013.01); *A61B 6/06* (2013.01)

(58) Field of Classification Search
CPC ..................................................... A61B 6/481
See application file for complete search history.

(56) References Cited

U.S. PATENT DOCUMENTS

| 2004/0028694 A1* | 2/2004 | Young | A61K 9/5169 |
| | | | 424/190.1 |
| 2009/0087383 A1* | 4/2009 | Bonitatibus, Jr. | |
| | | | A61K 49/0423 |
| | | | 424/9.42 |
| 2011/0052496 A1* | 3/2011 | Cid-Arregui | A61K 9/5184 |
| | | | 424/9.1 |

OTHER PUBLICATIONS

"X-ray spatial harmonic imaging of phase objects" by Y. Liu et al. Optics Letters. vol. 36, No. 12. Jun. 15, 2011.*
(Continued)

*Primary Examiner* — Tse W Chen
*Assistant Examiner* — Jason M Ip
(74) *Attorney, Agent, or Firm* — Adler Pollock & Sheehan P.C.

(57) ABSTRACT

Systems, compositions, methods and kits employ protein shells, such as ferritin or viral capsid shells, herein called nanobubbles, to enhance X-ray images of cells or body tissue under certain x-ray imaging methods. The nanobubbles have sub-micron size such as about 10 nm, about 40, 60, or 100 nm and may be functionalized for effective delivery to or uptake by a target tissue, in vivo or a cell culture. The nanobubbles are hollow, having a central core which may be empty or contain a fluid, such that the shells effectively form long-lived bubbles in the imaged environment, and are of low electron density and have different scattering properties than the surrounding tissue. X-ray imaging by spatial frequency heterodyne imaging enhances visualization or detection of tissue regions bearing the shells. The protein shells may be further treated to assure biocompatibility and/or to resist undesired interactions with non-targeted tissue, such as scavenging by the liver, or attack by the immune system. For example the nanobubbles may be filled with a hydrophobic gas such as perfluoropropane (octafluoropropane) to maintain their shape and resist hydrophilic interactions and delay the degradation of the (Continued)

protein shells. The nanobubbles may also be coated or treated by a surface-functionalization processes to effectively target specific tissues or tumor types, allow parenteral delivery, and/or deliver drugs or other agents to the imaged sites—so that when visualized by X-ray scatter imaging the presence of the nanobubbles indicates the existence and extent of the tumor or diseased tissue.

18 Claims, 3 Drawing Sheets (51) Int. Cl.
    *A61B 6/00*     (2006.01)
    *A61K 49/04*    (2006.01)

(56) References Cited

OTHER PUBLICATIONS

"Sheltering DNA in self-organizing, protein-only nano-shells as artificial viruses for gene delivery" by U. Unzueta et al. Nanomedicine: Nanotechnology, Biology, and Medicine. 10. 535-541. 2014.*
"Nanocarriers as an emerging platform for cancer therapy" by D. Peer et al. Nature Nanotechnology. vol. 2. 2007.*
"X-ray spatial frequency heterodyne imaging" by B. Wu et al. Applied Physics Letters. 100. 061110. 2012.*
Garimella et al. "Multivalent, high-relaxivity MRI contrast agents using rigid cysteine-reactive gadolinium complexes" J. Am. Chem. Soc. 2011, 133, 14704-14709.
Li et al. "Viruses and their potential in bioimaging and biosensing applications" Analyst 2010, 135, 21-27.
Liepold "Supramolecular protein cage composite MR contrast agents with extremely efficient relaxivity properties." Nano Letters 2009, 9, 4520-4526.
Lucon et al. "Use of the interior cavity of the P22 capsid for site-specific initiation of atom-transfer radical polymerization with high-density cargo loading" Nature Chemistry 2012, 4, 781-788.
Rand et al. "Nanomaterials for X-ray imaging: gold nanoparticle enhancement of X-ray scatter imaging of hepatocellular carcinoma" Nano Letters 2011, 11, 2678-2683.
Shen et al. "Materials design using genetically engineered proteins" A. J. Mater. Chem. 2011, 21, 18868-18876.
Uchida et al. "Targeting of Cancer Cells with Ferrimagnetic Ferritin Cage Nanoparticles". Am. Chem. Soc. 2006, 128, (51), 16626-16633.
Uchida et al. "The ferritin super family: supramolecular templates for material synthesis" Biochimica et Biophysica Acta 2010, 1800, 834-845.
Wu et al. "X-ray spatial frequency heterodyne imaging" Applied Physics Letters 2012, 100, 061110.

* cited by examiner

TABLE 1

| 50 nm AuNP vs. P22 ES | | 50 nm AuNP vs. P22 EX | | 10 nm AuNP vs. Ferritin | |
|---|---|---|---|---|---|
| *50 nm AuNP* | 8.2 ± 0.35 | *50nm AuNP* | 8.2 ± 0.35 | *10nm AuNP* | 6.5 ± 0.43 |
| *P22 ES* | 7.1 ± 0.20 | *P22 EX* | 7.5 ± 0.14 | *Ferritin* | 6.7 ± 0.18 |
| *Sonicated P22 ES* | 1.0 ± 0.08 | *Sonicated P22 EX* | 1.6 ± 0.03 | *Sonicated Ferritin* | 0.0 ± >0.01 |
| *P22 ES shell* | 1.2 ± 0.22 | *P22 EX shell* | 0.2 ± 0.09 | *Ferritin shell* | 1.8 ± 0.21 |

FIGURE 4

TABLE 2

| | X-ray absorbance signal enhancement (%) | X-ray scatter signal enhancement (%) |
|---|---|---|
| *P22 ES* | 0.14 ± 0.003 | 7.1 ± 0.20 |
| *P22 EX* | 0.09 ± 0.001 | 7.5 ± 0.14 |
| *Ferritin* | 0.15 ± 0.001 | 6.6 ± 0.18 |

FIGURE 5

TABLE 3

| Contrast Agent (1 mg/mL) | Concentration by number (particles/mL) |
|---|---|
| *50 nm AuNP* | $7.9 \times 10^{11}$ |
| *10 nm AuNP* | $9.9 \times 10^{13}$ |
| *P22 ES nanobubble* | $3.1 \times 10^{13}$ |
| *P22 EX nanobubble* | $3.1 \times 10^{13}$ |
| *Ferritin nanobubble* | $1.3 \times 10^{15}$ |

FIGURE 6

PROTEIN-BASED NANOBUBBLE X-RAY IMAGING METHOD AND AGENT

RELATED APPLICATION

This application is related to and claims the priority of Provisional U.S. Patent Application Ser. No. 61/981,945 filed on Apr. 21, 2014 in the United States Patent and Trademark Office.

GOVERNMENT FUNDING

This invention was made with government support under DE-FG02-08ER15937 awarded by the Department of Energy and contract number R01 EB012027 awarded by the National Institutes of Health. The Government has certain rights in the invention.

BACKGROUND

This invention relates to enhancement of x-ray images, and in particular to the enhancement of imaging capabilities using spatial heterodyne image processing to enhance visualization of a target tissue.

One of the co-inventors herein, Christoph Rose-Petruck, has previously performed scatter-imaging experiments with gold-based nanoparticle enhancement agents, which are reported in U.S. patent application Ser. No. 13/645,938, published with publication number 2013/0095499A1 on Apr. 18, 2013. That patent application is also incorporated herein by reference in its entirety for its discussions of relevant background technology, techniques of sample preparation and nanoparticle treatment or functionalization or administration, and techniques of X-ray processing or imaging, inter alia. More specific information related to the present invention has now been published in an article entitled *X-ray Spatial Frequency Heterodyne Imaging of Protein-based Nanobubble Contrast Agents*, in Optics Express (2014) Vol. 22 No. 19. That article and its bibliography is also incorporated herein by reference for purposes of describing and enabling the invention and its equivalents as set forth below and in the claims.

SUMMARY OF THE INVENTION

Briefly, the inventors have made the surprising discovery, and verified by experiment, that small empty protein "nanobubbles" may be visualized by scatter X-ray imaging techniques, even though the nanoparticles are not loaded with conventional scattering or absorbing materials such as gold or other metal, and are in fact both small and formed of relatively non-distinctive biomaterial. As such, the nanobubbles constitute a completely degradable and essentially nontoxic agent safe for parenteral or other administration to enhance contrast and discrimination among features of imaged tissue, and to enable early diagnostic detection of target tissue features using commonly available clinical X-ray instrumentation.

DETAILED DESCRIPTION

Spatial Frequency Heterodyne Imaging (herein abbreviated SFHI) is a recent x-ray scatter imaging technique in its application to nanoparticle contrast agents. Previous SFHI studies which address nanoparticles as potentially imageable scatterers have utilized only metal nanoparticle contrast agents, often having a crystal microstructure and with a high electron density. Applicants have now found that nanomaterials with a much lower density are also suitable. Proof-of principle investigations implementing the invention are reported below, and demonstrate that protein shells of small size—protein-based "nanobubble" contrast agents that are comprised of protein cage structures filled with gas can be effectively imaged. Results show that, by weight, these nanobubbles provide contrast in SFHI comparable to or better than that of gold nanoparticles of similar size.

The SFHI x-ray imaging technique as developed in recent years has used x-rays scattered by a sample to form an image. The scatterers may be natural structures within an imaged specimen, such as mineralized or oriented structure in plant material, or may rely upon scatterers introduced to render a target susceptible to scatter imaging. See Wen, H.; Bennett, E. E.; Hegedus, M. M.; Carroll, S. C. *IEEE Trans Med Imaging* 2008, 27, 997-1002; Wen, H.; Bennett, E. E.; Hegedus, M. M.; Rapacchi, S. *Radiology* 2009, 251, 910-918; Stein, A. F.; Ilavsky, J.; Kopace, R.; Bennett, E. E.; Wen, H. *Optics Express* 2010, 18, 13271-13278; Wu, B.; Liu, Y.; Rose-Petruck, C.; Diebold, G. *J. Applied Physics Letters* 2012, 100, 061110.

SFHI is based on a linear arrangement of x-ray source, tissue, and x-ray detector, much like that of a conventional x-ray imaging apparatus. However, SFHI rests on a complete paradigm reversal compared to conventional x-ray absorption-based radiology, which conventionally rejects or blocks scattered x-rays to enhance the image contrast. However when imaging body tissue, only hard tissue is highly absorptive; soft tissue is of low contrast. The invention herein applies SFHI to enhance the scattered x-ray signal, and remove the transmission/absorption component from the detected image data. Benefits of SFHI compared to absorption-based x-ray imaging include its improved sensitivity and its ability to yield anisotropic information regarding how the object being imaged scatters incident x-rays. See Liu, Y.; Ahr, B.; Linkin, A.; Diebold, G. J.; Rose-Petruck, C. *Optics Letters* 2011, 36, (12), 2209-2211; Rand, D.; Ortiz, V.; Liu, Y.; Derdak, Z.; Wands, J. R.; Taticek, M.; Rose-Petruck, C. *Nano Letters* 2011, 11, 2678-2683.

The use of gold and iron oxide nanoparticle contrast agents has been demonstrated to further enhance the sensitivity of SFHI (Stein et al, 2010, supra and Rand et al, 2011, supra). Specifically, gold nanoparticles —AuNPs- have been utilized as SFHI contrast agents for the imaging of human Hepatocellular Carcinoma, with results demonstrating that SFHI is capable of distinguishing between cancer tissue labeled with AuNPs and tissue that has not been so labeled. Ibid. Until quite recently, this application of SFHI for biomedical imaging was centered on the idea that the increased electron density of the metal nanoparticle contrast agents (relative to typical biological tissues) was required to improve the visibility of nanoparticle-targeted tissues in SFHI x-ray scatter images.

However, the inventors have now discovered that high electron density materials are not a necessary precondition for providing contrast in SFHI. Rather, the only requirement for an x-ray scatter contrast agent to be useful in biomedical imaging applications is that the electron density that differs from that of the biological tissues being studied. Thus, a wide variety of different types of nanoparticles including those with very low electron density are believed to be suitable for developing SFHI. This disclosure describes proof of principle experiments with development of a novel protein-based nanoparticle contrast agent comprised of nano-sized protein cage architectures that are filled with perfluoropropane ($C_3F_8$) gas.

Applicants have used several different protein assemblies to make these "nanobubble" contrast agents for SFHI experimentation. These were apoferritin, forming spherical shells approximately 12 nm outer diameter (see Uchida, M.; Kang, S.; Reichhardt, C.; Harlen, K.; Douglas, T. *Biochimica et Biophysica Acta* 2010, 1800, 834-835); and a virus-like particle (VLP) derived from the *Salmonella typhimurium* bacteriophage P22 capsid, approximately 60 nm outer diameter (see, Lucon, J.; Qazi, S.; Uchida, M.; Bedwell, G. J.; LaFrance, B.; Prevelige, P. E.; Douglas, T. *Nature Chemistry* 2012, 4, 781-788; Patterson, D. P.; Prevelige, P. E.; Douglas, T. *ACS Nano* 2012, 6, (6), 5000-5009; Patterson, D. P.; Schwarz, B.; El-Boubbou, K.; van der Oost, J.; Prevelige, P. E.; Douglas, T. *Soft Matter* 2012, 8, 10158-10166; and Patterson, D. P.; Rynda-Apple, A.; Harmsen, A. L.; Harmsen, A. G.; Douglas, T. *ACS Nano* 2013, 7, (4), 3036-3044).

The specific protein cage structures mentioned above are available for experimentation, as they have been studied for their potential in fields such as materials synthesis (see, Uchida et al, 2010, supra; and Douglas, T.; Young, M. *Nature* 1998, 393, 152-155); such as catalysis (see, Kang, S.; Douglas, T. *Science* 2010, 327, 42-43; and Worsdorfer, B.; Woycechowsky, K. J.; Hilvert, D. *Science* 2011, 331, 589-592); such as drug and gene delivery (see, Flenniken, M. L.; Liepold, L. O.; Crowley, B. E.; Willits, D. A.; Young, M. J.; Douglas, T. *Chem. Commun.* 2005, 447-449; and Ren, Y. P.; Wong, S. M.; Lim, L. Y. *Pharm. Res.* 2010, (27), 2509-2513; and such as MRI bio-imaging (see Liepold, L. O.; Abedin, M. J.; Buckhouse, E. D.; Frank, J. A.; Young, M. J.; Douglas, T. *Nano Letters* 2009, 9, 4520-4526; also Li, K.; Nguyen, H. G.; Lu, X. B.; Wang, Q. *Analyst* 2010, 135, 21-27; and Garimella, P. D.; Datta, A.; Romanini, D. W.; Raymond, K. N.; Francis, M. B. *J. Am. Chem. Soc.* 2011, 133, 14704-14709). They have also seen use in cell targeting (see, Flenniken, M. L.; Willits, D. A.; Harmsen, A. L.; Liepold, L. O.; Harmsen, A. G.; Young, M. J.; Douglas, T. *Chem. Biol.* 2006, 13, 161170; and Stephanopoulos, N.; Tong, G. J.; Hsiao, S. C.; Francis, M. B. *ACS Nano* 2010, 4, 6014-6020); and in vaccine development (see, Patterson et al 2013, supra).

VLPs in particular are promising, as they exist in a large range of sizes (tens to hundreds of nanometers), have well-defined, monodisperse structures, can be purified in large quantities, and can be easily modified both genetically and chemically. (See, for example, Douglas, T.; Young, M. *Science* 2006, 312, 873-875; Lee, L. A.; Wang, Q. *Nanomnedicine* 2006, 2, 137-149; Uchida, M.; Klein, M. T.; Allen, M.; Suci, P.; Flenniken, M.; Gillizter, F.; Varpness, Z.; Liepold, L. O.; Young, M.; Douglas, T. *Adv. Mater.* 2007, 19, 1025-1042; de la Escosura, A.; Nolte, R. J. M.; Cornelissen, J. J. L. M. *J. Mater. Chem.* 2009, 19, 2274-2278; Shen, L.; Bao, N.; Zhou, Z.; Prevelige, P. E.; Gupta, A. *J. Mater. Chem.* 2011, 21, 18868-18876; and Yildiz, I.; Shukla, S.; Steinmetz, N. F. *Current Opinions in Biotechnology* 2011, 22, 901-908).

The flexibility of such particles has facilitated the design of bionanomaterials with multiple functionalities via modification of the inner and outer capsid surfaces. For example, previous studies have shown that VLPs can both encapsulate various cargoes (including small molecules, polymers, enzymes, nanoparticles, and nucleic acids) and be surface-modified with antibodies, peptides, and other ligands. (see, Lee, L. A.; Niu, Z. W.; Wang, Q. *Nano Res.* 2009, 2, 349-365.) Reference is made to the aforesaid publications for the techniques useful for combining the imaging capabilities of the nanobubble contrast agents (as described herein) with tissue targeting and therapeutic functionalities that have been elucidated in the art which utilized such particles for other ends, such as for contrast agents based on protein cage architectures applied for other bio-imaging modalities. Examples include VLPs encapsulating fluorophores for fluorescence imaging and VLPs encapsulating gadolinium or iron oxide compounds for magnetic resonance imaging (MRI). (Uchida (2010) supra; Liepold, L. O.; Abedin, M. J.; Buckhouse, E. D.; Frank, J. A.; Young, M. J.; Douglas, T. *Nano Letters* 2009, 9, 4520-4526; Li, K.; Nguyen, H. G.; Lu, X. B.; Wang, Q. *Analyst* 2010, 135, 21-27; and Garimella, P. D.; Datta, A.; Romanini, D. W.; Raymond, K. N.; Francis, M. B. *J. Am. Chem. Soc.* 2011, 133, 14704-14709.

We have now evaluated the utility of such nanostructures for their imageability as contrast agents in x-ray scatter imaging. The experiments described below establish that effective visualization of scattered radiation by x-ray scatter image processing, even when employing nanoparticle agents of the types that have been proposed for other imaging modalities (MRI, fluorescence) can be successfully performed using nanoparticles lacking metallic or high-electron-density components. We refer to such nanoparticles as nanobubbles.

The nanobubble formulation as described herein may be analogized to a microbubble agent which has been used for the providing contrast in ultrasound imaging, for example, Optison, a commercially-available ultrasound contrast agent which consists of an aqueous suspension of 4 μm diameter albumin shells filled with perfluoropropane gas ($C_3F_8$)—see, Shen, L.; Bao, N.; Zhou, Z.; Prevelige, P. E.; Gupta, A. *J. Mater. Chem.* 2011, 21, 18868-18876. Optison has been shown to work as a contrast agent for SFHI—see Liu et al, 2011, supra; however, the size of the Optison bubbles limits their possible in vivo applications. Nano-sized protein-based contrast agents such as those described here could potentially be much more versatile and could be used for the in vivo targeting and imaging of individual cells, but their detectability has not been explored.

Methods and Materials

To prepare the protein-based nanobubble contrast agents, Human heavy-chain ferritin (HFn) and the procapsid (PC) form of P22 were heterologously expressed in *E. coli* BL21 (DE3) and purified as described in Lucon el al (2012) supra, and Uchida, M.; Flenniken, M.; Allen, M.; Willits, D. A.; Crowley, B. E.; Brumfield, S.; Willis, A. F.; Jackiw, L.; Julita, M.; Young, M. J.; Douglas, T. *J. Am. Chem. Soc.* 2006, 128, (51), 16626-16633. P22 scaffolding protein was extracted to prepare the empty shell (ES) form of P22 VLP using a buffer (50 mM sodium phosphate and 100 mM sodium chloride at pH 7.0) containing 0.5M of guanidine-HCl followed by ultracentrifugation of the capsid to pellet the capsid, which was subsequently resuspended in the same buffer. This extraction process was repeated four times. The expanded shell (Ex) form of the P22 VLP was prepared by heating the P22 procapsid at 65° C. for 20 min.—see Galisteo, M. L.; King, J. *Biophysical Journal* 1993, 65, 227-235.

Just prior to lyophilization, ferritin and P22 VLP (both ES and Ex forms) were dialyzed against water and a buffer (2 mM sodium phosphate and 30 mM sodium chloride at pH 7.4), respectively. One milliliter of each protein (2 mg/mL) was aliquoted into a glass vial, quickly frozen in a liquid nitrogen bath, and then lyophilized. The glass vials were sealed with a septum cap, and subject to evacuation and back-filling with $C_3F_8$ gas (at 1 atm) twice. While under $C_3F_8$ gas atmosphere, 0.4 mL of water was added to each vial via a syringe through the septum to reconstitute the lyophilized protein with gas trapped inside the protein cage.

For comparison, Gold nanoparticles (AuNPs) similar in size to the protein-based nanobubbles described above were prepared in aqueous suspension. 10 nm and 50 nm AuNPs in citrate buffer were purchased from British Biocell International (Cardiff, UK). Prior to x-ray imaging, AuNPs were stabilized with a coating of thiol-functionalized polyethylene glycol (PEG). O-(3-carboxypropyl)-O'-[2-(3-mercaptopropionylamino)ethyl]-polyethylene glycol (HS-PEG-COOH, $M_w$=3000) was purchased from Sigma-Aldrich (St. Louis, Mo.) and prepared at 100 μM in nanopure water. To 50 μg of as-purchased AuNPs in citrate buffer, 140 μL of PEG (for 10 nm AuNPs) or 28 μL of PEG (for 50 nm AuNPs) was added and stirred overnight at room temperature. The chains of functionalized PEG attach to the surface of the AuNPs during this mixing, replacing the citrate stabilizer due to the affinity of thiols for gold. Excess PEG was removed by centrifugation, and the resulting PEG-coated AuNPs were resuspended in ultrapure water.

For x-ray imaging, all samples were prepared in ultrapure water at concentrations of 1 mg scattering material/mL: AuNP samples (2 total) contained 1 mg Au/mL and protein nanobubble samples (9 total) contained 1 mg protein/mL. Samples were placed in a glass tube and held in an aluminum holder alongside a control sample which was a glass tube containing ultrapure water alone. Three x-ray absorbance and three x-ray scatter images were taken of each sample. Signals measured for the 11 samples were normalized relative to that measured for the water control. Results given in the text are the average and standard deviation of normalized signals measured over each set of three images.

The x-ray measurements were made using a microfocus X-ray tube (Trufocus Corp., model TFX-3110EW) with a tungsten anode. The tube was operated at an electrical power of 16 W, with a maximum voltage of 80 kV. High voltages are used to reduce required exposure times; they are also better suited for future applications requiring large penetration depths of human or animal subjects. The distance between the source and sample was 0.4 m, and the distance between the sample and detector was 1.2 m. The grid used is a nickel wire mesh with a pitch of approximately 170 μm. The grid was purchased from Small Parts, Inc. (Seattle, Wash.), and was positioned between the x-ray source and the sample, directly in front of the sample. The images were acquired with an x-ray CMOS detector (Rad-Icon Imaging, RadEye200 model). The total exposure time for each image was 180 seconds.

Figure 1:
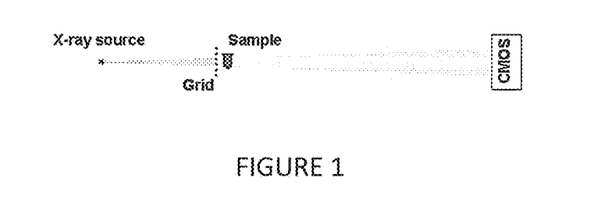
FIG. 1 is a schematic representation of the x-ray imaging setup for processing of the invention.

The x-ray imaging technique applied here, called Spatial Frequency Heterodyne Imaging (see references, supra) uses x-rays scattered by the sample to form an image. The object being imaged deflects incident x-rays from the primary beam direction, and this deflection can be detected by placing a grid between the sample and the x-ray detector, as shown schematically in FIG. 1. While FIG. 1 schematically shows an imaging set-up having a grid positioned between an X-ray source and an imaged target, it will be appreciated that the grid for spatial modulation of the x-rays may in various imaging environments also or alternatively be positioned between the target and the X-ray detector.

Without sample, the image of the grid is sharp and is limited only by the resolution of the imaging system. Introduction of the sample, however, yields scattered x-rays that cause a blurring of the grid image. The extent of this blurring corresponds to the amount of x-rays that are scattered by the sample, and is therefore a measure of nanoparticle concentration when such contrast agents are utilized. The imaging theory is discussed in Wu et al, 2012, supra. Acquired images are analyzed by a procedure involving Fourier transformation. The intensity modulations in an image taken of sample sandwiched with a grid are proportional to the product of the x-ray transmittances of the sample and of the grid. Thus, Fourier transformation of the image converts this product into a convolution in the spatial frequency domain.

Figure 2:
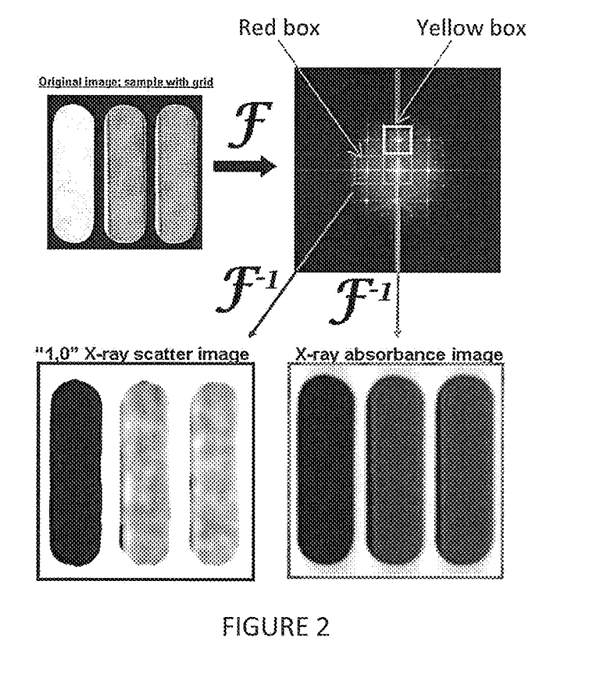
FIG. 2 illustrates Fourier transformation of an image with grid and sample placed in the x-ray beam path (top left) to give a convolution in the spatial frequency domain (top right), wherein different peaks in the spatial frequency spectrum (surrounded by boxes) contain different information regarding how the sample scatters and absorbs incident x-radiation.

This is illustrated in FIG. 2, schematically showing Fourier transformation of an image with grid and sample placed in the x-ray beam path (top left) to give a convolution in the spatial frequency domain (top right), wherein different peaks in the spatial frequency spectrum (surrounded by boxes) contain different information regarding how the sample scatters and absorbs incident x-radiation. The grid, a periodic structure, produces a series of peaks in this convolution, and each peak is surrounded by the spatial frequency spectrum of the sample. The areas surrounding all peaks in the convolution therefore contain the same information regarding x-ray transmittance through the sample. X-ray scatter does not influence the intensities around the central, zero-frequency peak, but does influence the intensities around all other higher order peaks. Selecting an area around the zero-order peak and an area around at least one other higher order peak and Fourier back-transforming these areas results in two separate images. The image $h_0$ from the zero-order area contains only x-ray transmittance information. The image $h_x$ from the higher order area contains both x-ray transmittance and x-ray scatter information. For normalization purposes, an image is acquired without sample and processed following the same Fourier procedure, resulting in one zero-order image $g_0$ and one higher-order image $g_x$ of the grid. Subsequently, a normalized absorbance image and one or more normalized scatter images are produced according to Equation 1 and Equation 2:

$$A = -\log_{10}\left(\frac{h_0}{g_0}\right) \quad (1)$$

$$S = -\log\left(\frac{h_x/g_x}{h_0/g_0}\right) \quad (2)$$

Thus, S consists exclusively of scattered x-rays because the transmittance component is normalized out. By convention, the absorbance A is defined as the logarithm of the ratio of the transmittances $h_0$ and $h_x$. The scattered intensity S is the logarithm of the amount of scattered radiation.

Experimental Results

To evaluate the feasibility and relative advantages of using nanobubbles as agents for x-ray scatter image enhancement, the foregoing imaging configuration and processing were applied to known gold nanoparticles and to protein shell nanobubbles.

Figure 3:
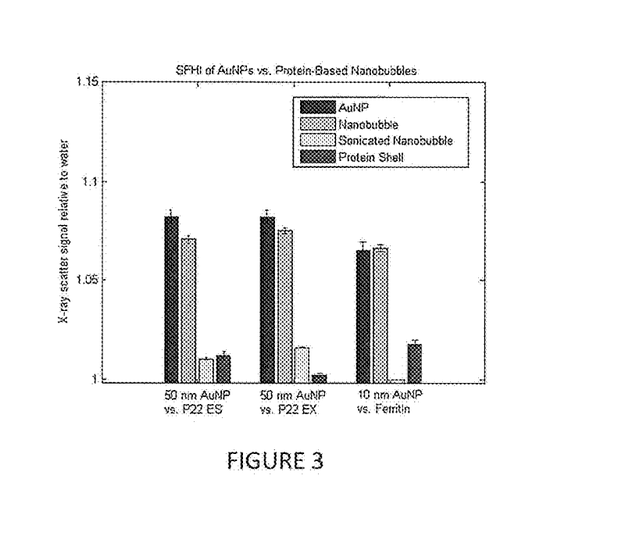
FIG. 3 shows SFHI x-ray scatter signal enhancements over water, comparing data for protein cage architectures and for gold nanoparticles of comparable size. Protein cages were imaged intact and filled with perfluoropentane gas (nanobubble formulation, light blue bars); after sonication (yellow bars) and intact but devoid of gas (red bars)
Figure 4:
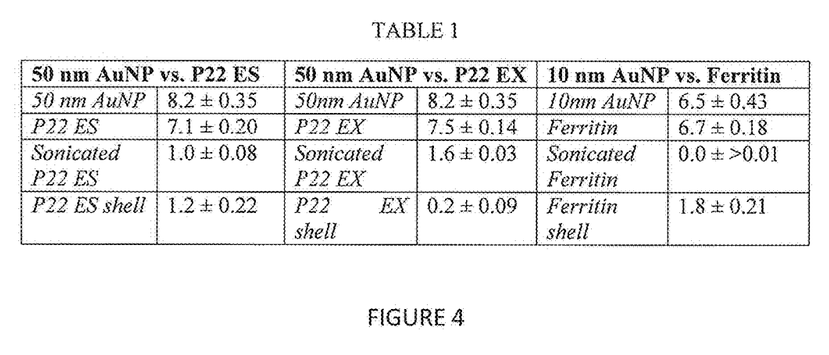
FIG. 4 is a table (TABLE 1) showing percentage SFHI image enhancement compared to H2O, for nanobubbles and to gold nanoparticles.

FIG. 3 illustrates the measurements thus made, showing the SFHI x-ray scatter signal enhancements over water for the protein cage architectures and for the gold nanoparticles of comparable size. Protein cages were imaged intact and filled with perfluoropentane gas (nanobubble formulation, light blue bars); were imaged after sonication (yellow bars) and were imaged intact but devoid of gas (red bars). The results are shown in TABLE 1, discussed below, for AuNP and VLP samples at a concentration of 1 mg scattering material/mL H2O.

The image processing concept is schematically depicted in FIG. 2. The zero-order peak (blue box) in the convolution yields the absorbance image A. The $1^{st}$ order peaks (red and yellow boxes) in the convolution yield the scatter images S. Note that the left $1^{st}$ order peak (red box) contains radiation scattered only in the horizontal direction; by convention we label this image the "1,0" scatter image after processing. Similarly, the upper $1^{st}$ order peak (yellow box) corresponds to scattering in the vertical direction, and gives a "0,1" scatter image after processing. Thus, every x-ray image taken yields three types of processed images; one corresponding to x-radiation absorbed by the sample, one corresponding to x-radiation scattered horizontally by the sample, and one corresponding to x-radiation scattered vertically by the sample. It should be noted that although this technique is capable of giving anisotropic scattering information, both $1^{st}$ order x-ray images should measure identical scatter signals when isotropically-oriented nanoparticles (such as the nanobubbles employed here) are used as SFHI contrast agents.

The three "nanobubble" contrast agents studied here were prepared from three different protein cage architectures. The smallest nanobubble was prepared using apoferritin, a protein cage with an outer diameter of approximately 12 nm and inner diameter of approximately 8 nm.

The larger nanobubbles were prepared using two distinct morphologies of a virus-like particle (VLP) derived from the *Salmonella typhimurium* bacteriophage P22 capsid. This VLP is a protein cage composed of 420 subunits of a 46.6 kDa coat protein that assemble into an icosahedral capsid with the aid of a scaffolding protein. (see the Lucon el al, and the three Patterson et al articles, supra. The first VLP morphology used here is the empty shell formulation of the VLP (P22 ES), in which the scaffolding protein has been removed; the resulting protein cage has an outer diameter of approximately 58 nm and an inner diameter of approximately 48 nm. The second VLP morphology used is the expanded shell formulation of the VLP (P22 EX), which is formed when gentle heating causes the VLP to expand to a protein cage with an outer diameter of approximately 64 nm and inner diameter of approximately 54 nm. To prepare the contrast agent, all three protein cage architectures were lyophilized, filled with perfluoropentane gas (C3F8) and resuspended in water. The hydrophobic gas remains trapped within the protein cages for at least several days and perhaps much longer. Further studies may be performed to determine the long-term stability of the contrast agents.

To analyze their ability to scatter x-rays, the three contrast agents were suspended in water at a concentration of 1 mg protein/mL and imaged by SFHI. A sample containing water alone was used as reference. Analysis of the images involved measuring the signals detected for containing only water. To compare the nanobubbles to contrast agents used previously in SFHI, samples containing gold nanoparticles of comparable size were also prepared at 1 mg Au/mL and imaged by SFHI. The contrast provided by the larger P22 nanobubbles was compared to that of 50 nm AuNPs, while the contrast provided by the smaller ferritin nanobubbles was compared to that of 10 nm AuNPs. The subsequent signal enhancements over water for both the nanobubbles and the AuNPs as measured from SFHI x-ray scatter images are reported as percentages in TABLE 1, which appears in FIG. 4.

The results indicate that when nanobubbles and AuNPs of similar sizes are prepared at equal concentrations by mass, they provide comparable contrast in SFHI, showing 6-8% x-ray scatter signal enhancement over water alone. The P22 EX nanobubbles are stronger x-ray scatterers than the P22 ES and ferritin nanobubbles by a small but statistically significant amount. This effect is likely due to the larger diameter of the P22 EX particles.

To prove that the contrast provided by the nanobubbles is due to the reduced electron density (relative to water) of the encapsulated gas, and not the scattering ability of the protein shell itself, the nanobubble samples discussed above were sonicated for 1 hour. Sonication should rupture the nanobubbles while leaving the elemental composition of the sample intact. Sonication causes the signal enhancement of the sample to drop 88% on average, from approximately 7% to less than 1% (see TABLE 1). Additionally, samples containing protein cages that had not been filled with gas (but retained their approximate size and shape) were suspended in water at 1 mg/mL and imaged by SFHI. The results show that these gasless samples also did not provide appreciable contrast in the resulting x-ray scatter images, showing an 84% drop on average relative to the gas-filled nanobubbles (TABLE 1). The data therefore suggest that only when the protein cages are intact and have encapsulated gas do they scatter x-rays in quantities comparable to that of gold nanoparticles of a similar size. See FIG. 3 which shows SFHI x-ray scatter signal enhancements over water for protein cage architectures and gold nanoparticles of comparable size. Protein cages were imaged intact and filled with perfluoropentane gas (nanobubble formulation, light blue bars); after sonication (yellow bars) and intact but devoid of gas (red bars).

Figure 5:
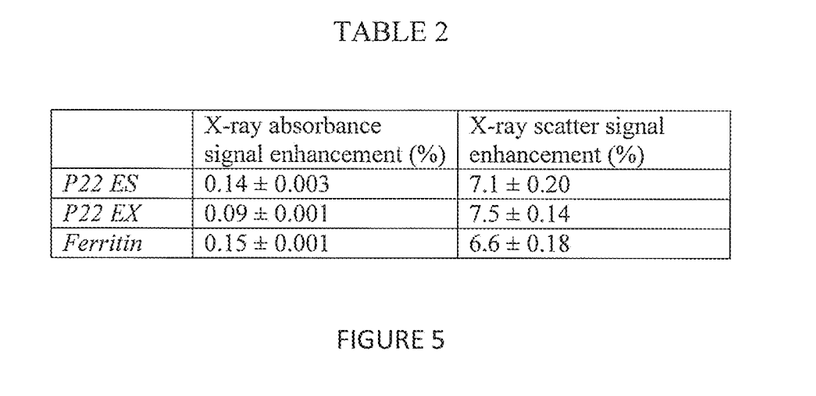
FIG. 5 is a table (TABLE 2) showing X-ray absorbance and x-ray scatter signal enhancements over water for nanobubble contrast agents prepared in water at 1 mg protein/mL.

It is also important to note that SFHI is much more sensitive to the contrast provided by the nanobubble contrast agents than conventional x-ray imaging. Absorption-based x-ray images were also taken of the three nanobubble contrast agents for comparison, and their signal enhancements relative to water are given as percentages in TABLE 2, shown in FIG. 5 which shows X-ray absorbance and x-ray scatter signal enhancements over water for nanobubble contrast agents prepared in water at a concentration of 1 mg protein/mL.

Figure 6:
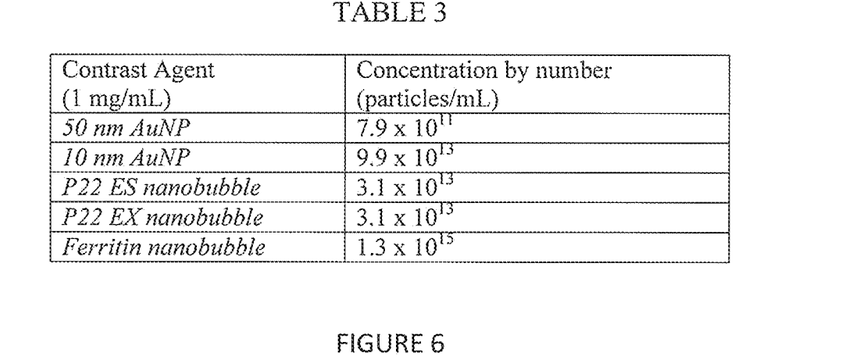
FIG. 6 is a table (TABLE 3) showing number densities of contrast agent samples prepared for imaging at 1 mg scattering material/mL.

FIG. 6 (TABLE 3) further shows number densities of contrast agent samples prepared for imaging at 1 mg scattering material/mL.

When x-ray absorbance images are compared to x-ray scatter images, we find that the x-ray scatter signal enhancements over water are greater than X-ray absorbance signal enhancements by an average factor of approximately 60.

The nanobubble x-ray contrast agents prepared here are the first of their kind. Results indicate that the contrast provided by this novel bionanomaterial in SFHI is comparable to that provided by AuNPs. We therefore expect that results obtained in the past using AuNP contrast agents in SFHI (for example, the differentiation of nanoparticle-labeled and unlabeled liver cancer tissue reported in Rand et al, 2011 supra) should be possible with nanobubbles as well. As such, the nanobubble contrast agents described herein could have many applications in diagnostic imaging and monitoring cancer growth.

We also contemplate combining the biomedical imaging function of the nanobubbles with other properties due to the flexibility of VLPs, as it is possible to modify both the inner and outer surfaces of these capsids. For example, VLPs have been targeted to specific cells including melanoma cells and lymphocytes by attaching antibodies and peptides to their outer surface. They have also been used for the delivery of chemotherapeutic agents such as the anticancer drug doxorubicin (see M. L. Flenniken et al, 2005) and photodynamic agents like singlet oxygen (see, Stephanopoulos et al, ACS Nano 4 (10), 6014-6020, (2010), both of which were encapsulated inside the protein cage.

Toxicity and immune response are issues to be addressed before clinical application, and these issues could be dealt with in part by modifying the outer surfaces of VLPs with polyethylene glycol (PEG), which has been shown to reduce bioactivity and increase the circulation time of nanoparticles in the bloodstream. Furthermore, VLPs are biocompatible and biodegradable, and they are considered non-infections and non-hazardous in humans. The fact that VLPs can be broken down in the body is important for their clinical application as contrast agents; this is especially true relative to AuNPs, which are nontoxic but can only be cleared from the body when they are smaller than approximately 5 nm in diameter. VLPs can also be purified in large quantities relatively inexpensively, which should make them cost-effective alternatives to the metal nanoparticle contrast agents used for SFHI in the past.

One important fact to note is that the nanobubbles and gold nanoparticles scatter x-rays in comparable amounts when prepared at the same concentration by mass (in this study, 1 mg scattering material/mL H2O). As gold nanoparticles are much denser than their nanobubble counterparts, however, an equal mass of gold and protein translates to a large discrepancy in the number of particles in the solution (see Table 3). We can therefore conclude that each individual AuNP scatters x-rays 10 to 20 times stronger than each individual protein-based nanobubble.

By mass, however, the nanobubbles described here appear to be just as effective as AuNPs when used as contrast agents in SFHI. Furthermore, we have shown that this scattering power derives not from the protein cage itself, but from the filling of the protein cage with gas. Our study has therefore proven that materials with both high and low electron density are capable of providing contrast in x-ray scatter imaging. This discovery improves the versatility of the novel x-ray imaging technique, as is it not specific any particular material for contrast, and when applied in vivo could utilize protein-based nanoparticles that may be more biocompatible than the metal nanoparticles used in the past. Furthermore, the enhanced sensitivity of SFHI relative to conventional absorption-based x-ray imaging is especially pronounced when VLPs are used as contrast agents; x-ray scatter signal enhancements over water are more than an order of magnitude greater than x-ray absorbance signal enhancements. Further tests and development of the nanobubble contrast agents (with modification of the inner and outer surfaces of the protein cages) could enable targeted diagnostic imaging and therapy.

The invention being thus disclosed and representative examples described, further variations and methods of making and using the invention will occur to those skilled in the art, as well as adaptations of the claimed nanobubble imaging technology to imaging, treatment, diagnostic and evaluation techniques familiar in the art, and all such embodiments are deemed to be included in and encompassed by the claims appended hereto and equivalents thereof.

What is claimed is:

1. A method of imaging cells or a tissue, the method comprising:
    providing to the cells or tissue, nanoparticles formed of protein, the nanoparticles having an outer diameter under about 60 nm disposed around a particle interior, the particle interior containing a hydrophobic material trapped or residing therein that prevents entry of aqueous material and thereby enhances stability of the nanoparticles in vivo, wherein the nanoparticles lack metal or other high Z coating, component or material that would otherwise increase x-ray transmission imaging contrast,
    irradiating the cells or the tissue with an X-ray source; and,
    X-ray scatter imaging the cells or the tissue with spatial frequency harmonic heterodyne image processing to effectively images regions of tissue or cells bearing the nano particles.

2. The method according to claim 1, wherein the nanoparticles are viral protein shells.

3. The method according to claim 1, wherein the nanoparticles are synthetic protein shells produced by recombinant production of a protein and self-assembly into shell structures.

4. The method according to claim 1, wherein the nanoparticles include protein shells comprising a virion coat protein or peptide.

5. The method according to claim 4, wherein the nanoparticles are protein shells that comprise a virion selected from the group consisting of: prokaryotic, protozoan, eukaryotic, virus-like particles, and bacteriophage virions, for example, wherein the virus shells are obtained from one selected from the group consisting of: Poxviridae, Entomopoxviridae, Baculoviridae, Eubaculovirinae, Nudibaculovirinae, Polydnaviridae, Ichnovirus, Iridoviridae, Bracovirus, Parvoviridae, Flavivirdae, Tagviridae, Bunyaviridae, Rhabdoviridae, Reoviridae, Bimaviridae, Picornaviridae, Tetraviridae and Nadoviridae.

6. The method according to claim 4, wherein the nanoparticle is a protein nanoshell that is semi-synthetic, is a synthetic peptide, or is a recombinantly produced protein.

7. The method according to claim 1, wherein the nanoparticles further comprise at least one material selected from the group consisting of: a polymer, a binding agent, and an organic material.

8. The method according to claim 1, wherein the hydrophobic material is or includes a hydrophobic gas such as perfluoropropane that excludes entry of aqueous.

9. The method according to claim 1, wherein irradiating the sample comprises locating or inserting an absorption grid adjacent to the sample between an X-ray source and a detector, and/or wherein imaging includes the step of positioning a grid between the sample and a detector and performing spatial frequency heterodyne image processing to selectively enhance regions of scattering by protein nanoparticles.

10. The method according to claim 1, wherein the nanoparticles comprise a binding agent that specifically binds the cells or the tissue, wherein the binding agent comprises at least one selected from the group of: a drug, a protein, a carbohydrate, and a nucleotide sequence.

11. The method according to claim 10, applied to tissue which comprises a plurality of cells in order to image or detect targeted cells selected from at least one of the group of: cancerous, non-cancerous, epithelial, hematopoietic, stem, spleen, kidney, pancreas, prostate, liver, neuron, breast, glial, muscle, sperm, heart, lung, ocular, brain, bone marrow, fetal, blood, leukocyte, and lymphocyte.

12. The method according to claim 10, applied to a tumor or cancer tissue selected from the group consisting of: melanoma; colon carcinoma; pancreatic; lymphoma; glioma; lung; esophagus; mammary; prostate; head; neck; ovarian; stomach; kidney; liver; and hepatocellular carcinoma.

13. The method according to claim 11, wherein the step of providing is performed by administering the nanoparticles parenterally.

14. The method according to claim 11, wherein the step of providing is performed by at least one route selected from the group consisting of: intra-tumoral, intravenous, intra-ocular, intra-muscular, subcutaneous, and intraperitoneal and oral.

15. The method according to claim 1 wherein the nanoparticles further include at least one fluid or contrast agent selected from the group consisting of: a magnetic resonance imaging (MRI) agent, a positive contrast agent, or a negative contrast agent, or, for example, an oil, a metal ion (e.g., iron and magnesium), or a metal compound.

16. A kit for imaging cells or a tissue, the kit comprising:
a plurality of nanoparticles that bind to and/or are taken up by the cells or the tissue, wherein the nanoparticles comprise a protein nano shell filled with a low electron density fluid and operable to function as empty protein nanoparticles visible with enhanced contrast by scatter X-ray imaging, the X-ray imaging with spatial frequency harmonic heterodyne image processing to effectively images regions of tissue or cells bearing the nano particles, the nanoparticles having an outer diameter under about 60 nm disposed around a particle interior, the particle interior containing a hydrophobic material trapped or residing therein that prevents entry of aqueous material and thereby enhances stability of the nanoparticles in vivo, wherein the nanoparticles lack metal or other high Z coating, component or material that would otherwise increase X-ray transmission imaging contrast.

17. The kit according to claim 16, wherein the protein shell comprises a viral protein shell or a protein shell, such as a virion coat protein or peptide, and optionally surrounds or is embedded in an exterior surface of at least one nanoparticle.

18. The kit according to claim 17, wherein the shell comprises a virion selected from the group consisting of: prokaryotic, protozoan, eukaryotic, virus-like particles, and bacteriophage virions or the shell is obtained from one selected from the group consisting of: Poxviridae, Entomopoxyviridae, Baculoviridae, Eubaculovirinae, Nudibaculovirinae, Polydnaviridae, Ichnovirus, Iridoviridae, Bracovirus, Parvoviridae, Flavivirdae, Tagviridae, Bunyaviridae, Rhabdoviridae, Reoviridae, Bimaviridae, Picornaviridae, Tetraviridae and Nadoviridae.

* * * * *